(12) United States Patent
Leussler et al.

(10) Patent No.: US 12,721,587 B2
(45) Date of Patent: Sep. 1, 2026

(54) MEDICAL SCAN APPARATUS

(71) Applicant: KONINKLIJKE PHILIPS N.V., Eindhoven (NL)

(72) Inventors: Christoph Günther Leussler, Hamburg (DE); Gereon Vogtmeier, Aachen (DE); Mark Thomas Johnson, Arendonk (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 56 days.

(21) Appl. No.: 18/857,326

(22) PCT Filed: Apr. 25, 2023

(86) PCT No.: PCT/EP2023/060798
§ 371 (c)(1),
(2) Date: Oct. 16, 2024

(87) PCT Pub. No.: WO2023/208927
PCT Pub. Date: Nov. 2, 2023

(65) Prior Publication Data

US 2025/0261922 A1 Aug. 21, 2025

(30) Foreign Application Priority Data

Apr. 28, 2022 (EP) .................................... 22170470

(51) Int. Cl.
*A61B 6/00* (2024.01)

(52) U.S. Cl.
CPC ................ *A61B 6/56* (2013.01); *A61B 6/545* (2013.01)

(58) Field of Classification Search
None
See application file for complete search history.

(56) References Cited

U.S. PATENT DOCUMENTS 7,360,100 B2 4/2008 Allred
2013/0181708 A1* 7/2013 Biber .................... G01R 33/36 324/318

(Continued)

OTHER PUBLICATIONS

PCT International Search Report, International application No. PCT/EP2023/060798, Jul. 28, 2023.

*Primary Examiner* — Hoon K Song
(74) *Attorney, Agent, or Firm* — Larry Liberchuk

(57) ABSTRACT

The present invention relates to a medical scan apparatus (10), comprising: an input unit (20); a processing unit (30); and an output unit (40). The input unit is configured to provide the processing unit with information regarding the power production capability of one or more power sources (60), and wherein a scan of a patient to be carried out by a medical imaging scanner (50) will utilize at least the one or more power sources. The processing unit is configured to predict the total energy that will be available to the medical imaging scanner over a time period, wherein the prediction comprises utilization of the information regarding the power production capability of the one or more power sources. The processing unit is configured to predict the instantaneous power that will be available to the medical imaging scanner during the time period, wherein the prediction comprises utilization of the information regarding the power production capability of the one or more power sources. The processing unit is configured to select a scan protocol for the medical imaging scanner to carry out the scan of the patient, wherein selection of the scan protocol comprises utilization of the predicted total energy that will be available to the medical imaging scanner over the time period and the predicted instantaneous power that will be available to the medical imaging scanner during the time period. The output unit is configured to provide the scan protocol to the medical imaging scanner.

11 Claims, 2 Drawing Sheets

(56) References Cited

U.S. PATENT DOCUMENTS

2019/0298285 A1* 10/2019 Rakic ...................... A61B 6/04
2022/0060046 A1* 2/2022 Biber .................... G01R 33/28
2025/0157639 A1* 5/2025 Thesen ................. G16H 50/30

* cited by examiner

MEDICAL SCAN APPARATUS

FIELD OF THE INVENTION

The present invention relates to a medical scan apparatus, a medical scan system, a medical scan method, as well as to a computer program element and a computer readable medium.

BACKGROUND OF THE INVENTION

Many hospitals worldwide suffer from unstable power-systems and variable power-conditions due to locations in rural areas and/or locations where the power network is not stable, which can negatively impact the operation of an imaging system, such as an attenuation X-ray system, computer tomography (CT) X-ray system or magnetic resonance (MR) imaging system, for example. Several companies offer vehicle based imaging solutions to be taken to remote places for scanning/screening of the population.

For the reliability and operation safety of an imaging system it is important to guarantee uptime which is related to an operational system and the operation condition which depends heavily on the electrical power network. This is essential in mobile settings and environments where power drops could happen and the system might be switched off due to unstable power conditions. Sometimes a generator and/or uninterruptable power supply could help but there is no prediction which scans on the imaging system could be done, could be finalized, or which scan conditions are compatible with the expected energy setting. This is because different scans have different energy requirements. This is even more critical for interventional procedures and/or therapeutic procedures.

Future hospital solutions are anticipated to consist of modular and mobile hospital services, where a fleet of mobile vehicles drive to different locations and support locally clinical needs with respect to diagnostic imaging, therapy, vaccination service, etc. This also applies to one or more mobile hospital ships. The discussion below, when referring to a vehicle or vehicles applies to both land/water based mobile platforms.

These vehicles are equipped in general with diagnostic systems which need energy for operation. The delivery of energy depends on the special location and situation. Typically these vehicles are equipped with generators using fuel. New upcoming energy sources are fuel cells combined with batteries and solar cells. Also heat pumps electrically driven, or other energy sources, can act as a supplement or replacement for an additional controlled generator or replacement or supplement for electrical heating for a diagnostic system. At rural hospitals and locations where an emergency situation has occurred, the delivery of energy is not always guaranteed. Local energy charging stations may not deliver the required constant power or energy generation.

The energy consumption of diagnostic scanning and a therapy session needs to be guaranteed during the application to finalize the procedure with guaranteed clinical quality. Also imaging quality can be affected and/or the operation of subsystems can not have the required reliability to finalize a diagnostic scan with a defined/required image quality.

However in mobile and rural situations this cannot be guaranteed and this may result in scans terminating prematurely and/or imaging quality not meeting requirements.

There is a need to address these issues.

SUMMARY OF THE INVENTION

It would be advantageous to provide an improved technique to facilitate the scanning of patients in locations where power and energy supply may be problematic.

The object of the present invention is solved with the subject matter of the independent claims, wherein further embodiments are incorporated in the dependent claims. It should be noted that the following described aspects and examples of the invention apply to the medical scan apparatus, the medical scan system, the medical scan method, as well as to a computer program element and a computer readable medium.

In a first aspect, there is provided a a medical scan apparatus, comprising:

an input unit;

a processing unit; and an output unit.

The input unit is configured to provide the processing unit with information regarding the power production capability of one or more power sources. A scan of a patient to be carried out by a medical imaging scanner will utilize at least the one or more power sources. The processing unit is configured to predict the total energy that will be available to the medical imaging scanner over a time period, and the prediction comprises utilization of the information regarding the power production capability of the one or more power sources. Additionally or alternatively the processing unit is configured to predict the instantaneous power that will be available to the medical imaging scanner during the time period, and the prediction comprises utilization of the information regarding the power production capability of the one or more power sources. The processing unit is configured to select a scan protocol for the medical imaging scanner to carry out the scan of the patient, and selection of the scan protocol comprises utilization of the predicted total energy that will be available to the medical imaging scanner over the time period and/or the predicted instantaneous power that will be available to the medical imaging scanner during the time period. The output unit is configured to provide the scan protocol to the medical imaging scanner.

In an example, the processing unit is configured to predict the total energy and/or instantaneous power utilized by the medical imaging scanner for a scan and/or or a scan sequence of a scan protocol.

In an example, the input unit is configured to provide the processing unit with information regarding the total energy utilized or required by the medical imaging scanner for a scan and/or or a scan sequence of a scan protocol.

In an example, the input unit is configured to provide the processing unit with information regarding the instantaneous power utilized or required by the medical imaging scanner for a scan and/or or a scan sequence of a scan protocol.

Thus, historical information of energy usage and power usage of the medical imaging scanner can be utilized, and/or reference material such as manufacturer and database information regarding power and energy drawn by the medical imaging scanner during a scan and/or scan sequence can be utilized. This means that historical information relating to for example the energy required for scan, and the energy required for image processing can be separated to some extent, enabling workflow to be separated into modules that require certain energy and into some modules that can be operated with some delay in the sequence instead of operating in parallel.

In an example, selection of the scan protocol comprises an increase in a total time of the scan.

In this way more energy is available.

In an example, selection of the scan protocol comprises an increase in time of a section of the scan.

In this way an instantaneous power requirement can be decreased to match that available.

In an example, selection of the scan protocol comprises a selected ordering of steps of the scan.

In this manner, a peak protocol power requirement can match peak available power.

In an example, selection of the scan protocol comprises a modification of one or more steps of the scan.

In other words, steps can be modified to use less power, that will then still provide useable data, but may not be "gold" standard if more power was used. Thus peak power used can match that predicted to be available.

In an example, the information regarding the power production capability of the one or more power sources comprises the instantaneous power production capability of one or more power sources.

Thus, instantaneous peak power can be delivered by electronically switching/connecting battery power banks or charged capacitor banks or by external connection of latter devices (hold ready) to the local smart grid. The smart grid can then provide details on the instantaneous power available right now from the one or more power sources, and that can be used to predict the total energy that will be available over a coming time period and the instantaneous power available over that time period.

In an example, the information regarding the power production capability of the one or more power sources comprises historical instantaneous power production capability of the one or more power sources.

In an example, the input unit is configured to provide the processing unit with weather forecast information. The prediction of the total energy that will be available to the medical imaging scanner over the time period can then comprise utilization of the weather forecast information, and the prediction of the instantaneous power that will be available to the medical imaging scanner during the time period can then comprise utilization of the weather forecast information.

In an example, the input unit is configured to provide the processing unit with historical weather information. The prediction of the total energy that will be available to the medical imaging scanner over the time period can then comprise utilization of the historical weather information, and the prediction of the instantaneous power that will be available to the medical imaging scanner during the time period can then comprise utilization of the historical weather information.

In an example, the input unit is configured to provide the processing unit with information regarding local dependency on energy utilization, such as energy utilization patterns within a city. The prediction of the total energy that will be available to the medical imaging scanner over the time period can then comprise utilization of the information regarding local dependency on energy utilization, and the prediction of the instantaneous power that will be available to the medical imaging scanner during the time period can then comprise utilization of the information regarding local dependency on energy utilization.

Thus, information from external data suppliers on weather information related to energy prediction such as wind and solar information can be utilized as well as historical weather data that can be linked to energy requirements for example from air conditioning systems utilized when it is hot that can be used to predict how much energy and power will be required by the one or more power sources to provide power to devices other than the medical imaging scanner enabling the scanner to predict what energy and power will be available to the medical imaging scanner. Also, information on general energy utilization, and patterns, across for example a city within which the medical scan system is located can be utilized to predict how much and when power will be available.

In an example, the processing unit is configured to determine that an additional power source to the one or more power sources will be required to be utilized by the medical imaging scanner to carry out the scan of the patient. The determination comprises utilization of the predicted total energy that will be available to the medical imaging scanner over the time period In an example, the processing unit is configured to determine that an additional power source to the one or more power sources will be required to be utilized by the medical imaging scanner to carry out the scan of the patient. The determination comprises utilization of the predicted instantaneous power that will be available to the medical imaging scanner during the time period.

In an example, the processing unit is configured to determine that a power drain will be required to be disconnected from the one or more power sources during the time period. The determination comprises utilization of the predicted total energy that will be available to the medical imaging scanner over the time period.

In an example, the processing unit is configured to determine that a power drain will be required to be disconnected from the one or more power sources during the time period. The determination comprises utilization of the predicted instantaneous power that will be available to the medical imaging scanner during the time period.

In an example, a trained neural network is utilized by the processing unit to predict the total energy that will be available to the medical imaging scanner over the time period and to predict the instantaneous power that will be available to the medical imaging scanner during the time period.

In an example, a trained neural network is utilized by the processing unit to select the scan protocol for the medical imaging scanner to carry out the scan of the patient.

In an example, a trained neural network is utilized by the processing unit to predict the total energy and/or instantaneous power utilized by the medical imaging scanner for a scan and/or or a scan sequence of a scan protocol.

In a second aspect, there is provided a medical scan system, comprising:

an input unit;

a processing unit; and a medical imaging scanner.

The input unit is configured to provide the processing unit with information regarding the power production capability of one or more power sources and wherein a scan of a patient to be carried out by the medical imaging scanner will utilize at least the one or more power sources. The processing unit is configured to predict the total energy that will be available to the medical imaging scanner over a time period, and the prediction comprises utilization of the information regarding the power production capability of the one or more power sources. Additionally or alternatively the processing unit is configured to predict the instantaneous power that will be available to the medical imaging scanner during the time period, and the prediction comprises utilization of the information regarding the power production capability of the one or more power sources. The processing unit is configured to select a scan protocol for the medical imaging scanner to carry out the scan of the patient. the selection of the scan protocol comprises utilization of the predicted total energy that will be available to the medical imaging scanner over the time period and/or the predicted instantaneous power that will be available to the medical imaging scanner during the time period. The processing unit is configured to provide the scan protocol to the medical imaging scanner.

It is to be noted that the medical imaging scanner can be formed from a number of units, such as a scan unit, and an image processing unit. The selected scan protocol for the medical imaging scanner can involve a selection of what scans are conducted when, but can also involve a selection of when different units of the medical imaging scanner operate. Thus, a determination can be made that not all the units of the medical imaging scanner operate at the same time, thus imaging processing need not be carried out at the same time as scanning in order to save power and energy at a time when it has been determined that there will be insufficient power and/or energy.

In a third aspect, there is provided a medical scan method, comprising:

- providing a processing unit with information regarding the power production capability of one or more power sources, and wherein a scan of a patient to be carried out by a medical imaging scanner will utilize at least the one or more power sources;
- predicting by the processing unit the total energy that will be available to the medical imaging scanner over a time period, wherein the predicting comprises utilizing the information regarding the power production capability of the one or more power sources; and/or
- predicting by the processing unit the instantaneous power that will be available to the medical imaging scanner during the time period, wherein the predicting comprises utilizing the information regarding the power production capability of the one or more power sources;
- selecting by the processing unit a scan protocol for the medical imaging scanner to carry out the scan of the patient, wherein selecting the scan protocol comprises utilizing the predicted total energy that will be available to the medical imaging scanner over the time period and/or the predicted instantaneous power that will be available to the medical imaging scanner during the time period; and
- providing the scan protocol to the medical imaging scanner.

The following provides several examples of how the new method can operation. Thus, for example an examination or a therapy session for a patient consists of at least one scan. Typically the imaging scan parameters are calculated in advance to get an image with a defined signal to noise ratio and contrast. If a scan needs to be interrupted due to upcoming lack of energy, the scan can be resumed at a later time step, when there is enough energy for stable operation. For the therapy session, dose is calculated in advance. For a 3D dose session (MR LINAC), the session can be interrupted when there is an upcoming predicted shortfall in energy/power, but can be resumed with a certain time delay (to a time when there is extra power, and/or after connection of extra energy storage). Thus, the selection of protocol and tuning of protocol segments due to energy prediction can be made but always carried out with diagnostic image quality of the required task as an optimization goal (but where, if necessary and what could constitute a worst case), with the overall scan being delayed.

According to aspects, there is provided computer program elements controlling one or more of the apparatuses and/or systems as previously described which, if the computer program element is executed by a processor, is adapted to perform the method as previously described.

According to other aspects, there is provided computer readable media having stored the computer elements as previously described.

The computer program element can for example be a software program but can also be a FPGA, a PLD or any other appropriate digital means.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

Figure 1:
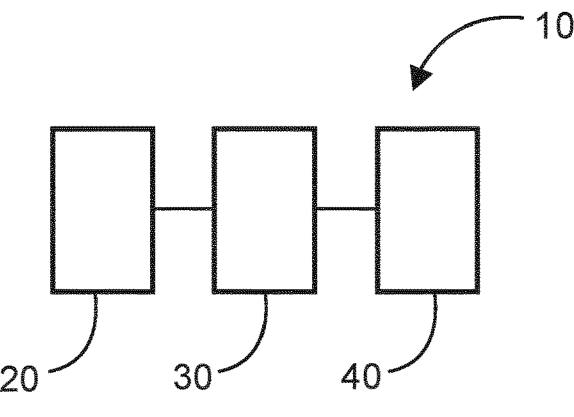
FIG. 1 shows a schematic representation of medical scan apparatus.

FIG. 1 shows an example of a medical scan apparatus 10. The apparatus 10 comprises an input unit 20, a processing unit 30, and an output unit 40. The input unit is configured to provide the processing unit with information regarding the power production capability of one or more power sources 60. A scan of a patient to be carried out by a medical imaging scanner 50 will utilize at least the one or more power sources. The processing unit is configured to predict the total energy that will be available to the medical imaging scanner over a time period. The prediction of the total energy that will be available to the medical imaging scanner over the time period comprises utilization of the information regarding the power production capability of the one or more power sources. Additionally or alternatively the processing unit is configured to predict the instantaneous power that will be available to the medical imaging scanner during the time period. The prediction of the instantaneous power that will be available to the medical imaging scanner during the time period comprises utilization of the information regarding the power production capability of the one or more power sources. The processing unit is configured to select a scan protocol for the medical imaging scanner to carry out the scan of the patient. The selection of the scan protocol comprises utilization of the predicted total energy that will be available to the medical imaging scanner over the time period and/or the predicted instantaneous power that will be available to the medical imaging scanner during the time period. The output unit is configured to provide the scan protocol to the medical imaging scanner.

According to an example, the processing unit is configured to predict the total energy utilized by the medical imaging scanner for a scan and/or or a scan sequence of a scan protocol. Additionally or alternatively the processing unit is configured to predict the instantaneous power utilized by the medical imaging scanner for a scan and/or or a scan sequence of a scan protocol.

According to an example, the input unit is configured to provide the processing unit with information regarding the total energy utilized or required by the medical imaging scanner for a scan and/or or a scan sequence of a scan protocol.

According to an example, the input unit is configured to provide the processing unit with information regarding the instantaneous power utilized or required by the medical imaging scanner for a scan and/or or a scan sequence of a scan protocol.

According to an example, the selection of the scan protocol comprises an increase in a total time of the scan.

According to an example, the selection of the scan protocol comprises an increase in time of a section of the scan.

According to an example, the selection of the scan protocol comprises a selected ordering of steps of the scan.

According to an example, the selection of the scan protocol comprises a modification of one or more steps of the scan.

The modification of one or more steps of the scan can include introducing time delays between steps.

According to an example, the information regarding the power production capability of the one or more power sources comprises the instantaneous power production capability of one or more power sources.

According to an example, the information regarding the power production capability of the one or more power sources comprises historical instantaneous power production capability of the one or more power sources.

According to an example, the input unit is configured to provide the processing unit with weather forecast information. The prediction of the total energy that will be available to the medical imaging scanner over the time period can then comprise utilization of the weather forecast information, and the prediction of the instantaneous power that will be available to the medical imaging scanner during the time period can then comprise utilization of the weather forecast information.

According to an example, the input unit is configured to provide the processing unit with historical weather information. The prediction of the total energy that will be available to the medical imaging scanner over the time period can then comprise utilization of the historical weather information, and the prediction of the instantaneous power that will be available to the medical imaging scanner during the time period can then comprises utilization of the historical weather information.

In an example, the input unit is configured to provide the processing unit with information regarding local dependency on energy utilization, such as energy utilization patterns within a city. The prediction of the total energy that will be available to the medical imaging scanner over the time period can then comprise utilization of the information regarding local dependency on energy utilization, and the prediction of the instantaneous power that will be available to the medical imaging scanner during the time period can then comprise utilization of the information regarding local dependency on energy utilization.

According to an example, the processing unit is configured to determine that an additional power source to the one or more power sources will be required to be utilized by the medical imaging scanner to carry out the scan of the patient, and the determination comprises utilization of the predicted total energy that will be available to the medical imaging scanner over the time period.

Additionally or alternatively the determination that an additional power source to the one or more power sources will be required to be utilized by the medical imaging scanner to carry out the scan of the patient comprises utilization of the predicted instantaneous power that will be available to the medical imaging scanner during the time period.

According to an example, the processing unit is configured to determine that a power drain will be required to be disconnected from the one or more power sources during the time period, and the determination comprises utilization of the predicted total energy that will be available to the medical imaging scanner over the time period. Additionally or alternatively the determination that a power drain will be required to be disconnected from the one or more power sources during the time period comprises utilization of the predicted instantaneous power that will be available to the medical imaging scanner during the time period.

Thus, for example other equipment in a hospital could be disconnected (if allowed) from the energy network before the scan and/or during the scan/and/or in an emergency situation when energy availability becomes critical during the scan despite planning. Thus, for example a decision can be made that for an upcoming scan or section of that scan no fridge and no air compression should be available during the scan to ensure that the necessary energy/power is available for the scan.

According to an example, a trained neural network is utilized by the processing unit to predict the total energy that will be available to the medical imaging scanner over the time period and to predict the instantaneous power that will be available to the medical imaging scanner during the time period.

According to an example, a trained neural network is utilized by the processing unit to select the scan protocol for the medical imaging scanner to carry out the scan of the patient.

In an example, the trained neural network that predicts total energy and instantaneous energy availability is the same neural network that selects the scan protocol.

In an example, a trained neural network is utilized by the processing unit to predict the total energy and/or instantaneous power utilized by the medical imaging scanner for a scan and/or or a scan sequence of a scan protocol.

The total energy and/or instantaneous power utilized by the medical imaging scanner here also refers to sub-systems and sub-processes utilized/required by the medical imaging scanner, and the trained neural network predicts the energy and/or instantaneous power utilized by such sub-systems and processes.

Figure 2:
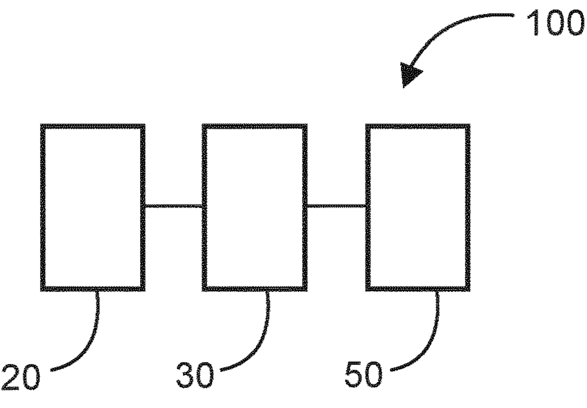
FIG. 2 shows a schematic representation of a medical scan system.

FIG. 2 shows an example of a medical scan system 100. The system 100 comprises an input unit 20, a processing unit 30, and a medical imaging scanner 50. The input unit is configured to provide the processing unit with information regarding the power production capability of one or more power sources 60. A scan of a patient to be carried out by the medical imaging scanner will utilize at least the one or more power sources. The processing unit is configured to predict the total energy that will be available to the medical imaging scanner over a time period, and the prediction comprises utilization of the information regarding the power production capability of the one or more power sources. Additionally or alternatively the processing unit is configured to predict the instantaneous power that will be available to the medical imaging scanner during the time period, and the prediction comprises utilization of the information regarding the power production capability of the one or more power sources. The processing unit is configured to select a scan protocol for the medical imaging scanner to carry out the scan of the patient, and selection of the scan protocol comprises utilization of the predicted total energy that will be available to the medical imaging scanner over the time period and/or the predicted instantaneous power that will be available to the medical imaging scanner during the time period. The processing unit is configured to provide the scan protocol to the medical imaging scanner.

In an example, the processing unit is configured to predict the total energy utilized by the medical imaging scanner for a scan and/or or a scan sequence of a scan protocol. Additionally or alternatively the processing unit is configured to predict the instantaneous power utilized by the medical imaging scanner for a scan and/or or a scan sequence of a scan protocol.

In an example, the input unit is configured to provide the processing unit with information regarding the total energy utilized or required by the medical imaging scanner for a scan and/or or a scan sequence of a scan protocol.

In an example, the input unit is configured to provide the processing unit with information regarding the instantaneous power utilized or required by the medical imaging scanner for a scan and/or or a scan sequence of a scan protocol.

In an example, the selection of the scan protocol comprises an increase in a total time of the scan.

In an example, the selection of the scan protocol comprises an increase in time of a section of the scan.

In an example, the selection of the scan protocol comprises a selected ordering of steps of the scan.

In an example, the selection of the scan protocol comprises a modification of one or more steps of the scan.

In an example, the information regarding the power production capability of the one or more power sources comprises the instantaneous power production capability of one or more power sources.

In an example, the information regarding the power production capability of the one or more power sources comprises historical instantaneous power production capability of the one or more power sources.

In an example, the input unit is configured to provide the processing unit with weather forecast information. The prediction of the total energy that will be available to the medical imaging scanner over the time period can then comprise utilization of the weather forecast information, and the prediction of the instantaneous power that will be available to the medical imaging scanner during the time period can then comprise utilization of the weather forecast information.

In an example, the input unit is configured to provide the processing unit with historical weather information. The prediction of the total energy that will be available to the medical imaging scanner over the time period can then comprise utilization of the historical weather information, and the prediction of the instantaneous power that will be available to the medical imaging scanner during the time period can then comprises utilization of the historical weather information.

In an example, the processing unit is configured to determine that an additional power source to the one or more power sources will be required to be utilized by the medical imaging scanner to carry out the scan of the patient, and the determination comprises utilization of the predicted total energy that will be available to the medical imaging scanner over the time period. Additionally or alternatively the determination that an additional power source to the one or more power sources will be required to be utilized by the medical imaging scanner to carry out the scan of the patient comprises utilization of the predicted instantaneous power that will be available to the medical imaging scanner during the time period.

In an example, the processing unit is configured to determine that a power drain will be required to be disconnected from the one or more power sources during the time period, and the determination comprises utilization of the predicted total energy that will be available to the medical imaging scanner over the time period. Additionally or alternatively the determination that a power drain will be required to be disconnected from the one or more power sources during the time period comprises utilization of the predicted instantaneous power that will be available to the medical imaging scanner during the time period.

In an example, a trained neural network is utilized by the processing unit to predict the total energy that will be available to the medical imaging scanner over the time period and to predict the instantaneous power that will be available to the medical imaging scanner during the time period.

In an example, a trained neural network is utilized by the processing unit to select the scan protocol for the medical imaging scanner to carry out the scan of the patient.

In an example, the trained neural network that predicts total energy and instantaneous energy availability is the same neural network that selects the scan protocol.

In an example, a trained neural network is utilized by the processing unit to predict the total energy and/or instantaneous power utilized by the medical imaging scanner for a scan and/or or a scan sequence of a scan protocol.

Figure 3:
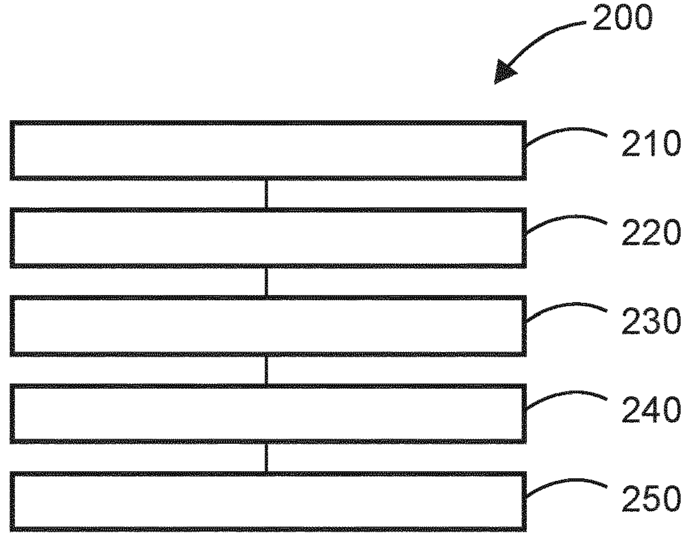
FIG. 3 shows a medical scan method.

FIG. 3 shows a medical scan method 200 in its basic steps. The method 200 comprises:

- providing 210 a processing unit with information regarding the power production capability of one or more power sources, and wherein a scan of a patient to be carried out by a medical imaging scanner will utilize at least the one or more power sources;
- predicting 220 by the processing unit the total energy that will be available to the medical imaging scanner over a time period, wherein the predicting comprises utilizing the information regarding the power production capability of the one or more power sources; and/or
- predicting 230 by the processing unit the instantaneous power that will be available to the medical imaging scanner during the time period, wherein the predicting comprises utilizing the information regarding the power production capability of the one or more power sources;
- selecting 240 by the processing unit a scan protocol for the medical imaging scanner to carry out the scan of the patient, wherein selecting the scan protocol comprises utilizing the predicted total energy that will be available to the medical imaging scanner over the time period and/or the predicted instantaneous power that will be available to the medical imaging scanner during the time period; and providing 250 the scan protocol to the medical imaging scanner.

In an example, selecting the scan protocol for the medical imaging scanner to carry out the scan of the patient comprises synchronising scan and energy availability.

In an example, the method comprises predicting by the processing unit the total energy and/or instantaneous power utilized by the medical imaging scanner for a scan and/or or a scan sequence of a scan protocol.

In an example, the method comprises providing the processing unit with information regarding the total energy and/or instantaneous power utilized or required by the medical imaging scanner for a scan and/or or a scan sequence of a scan protocol.

In an example, selecting the scan protocol comprises increasing a total time of the scan.

In an example, selecting the scan protocol comprises selecting an order of steps of the scan.

In an example, selecting the scan protocol comprises increasing a time of a section of the scan.

In an example, selecting the scan protocol comprises modifying one or more steps of the scan.

In an example, the information regarding the power production capability of the one or more power sources comprises the instantaneous power production capability of one or more power sources.

In an example, the information regarding the power production capability of the one or more power sources comprises historical instantaneous power production capability of the one or more power sources.

In an example, the method comprises providing the processing unit with weather forecast information, and the predicting the total energy that will be available to the medical imaging scanner over the time period comprises utilizing the weather forecast information, and the predicting the instantaneous power that will be available to the medical imaging scanner during the time period comprises utilizing the weather forecast information.

In an example, the method comprises provide the processing unit with historical weather information, and the predicting the total energy that will be available to the medical imaging scanner over the time period comprises utilizing the historical weather information, and the predicting the instantaneous power that will be available to the medical imaging scanner during the time period comprises utilizing the historical weather information.

Thus, for example a determination can be made that a scan should not be made before 9:00 or when scanning in March only to scan between 10:00 and 15:00, but not over lunch 11:30 to 13:00 when the weather is cloudy.

In an example, the method comprises determining by the processing unit that an additional power source to the one or more power sources will be required to be utilized by the medical imaging scanner to carry out the scan of the patient, and the determining comprises utilizing predicted total energy that will be available to the medical imaging scanner over the time period and/or the predicted instantaneous power that will be available to the medical imaging scanner during the time period.

In an example, the method comprises determining by the processing unit that a power drain will be required to be disconnected from the one or more power sources during the time period, and the determining comprises utilizing predicted total energy that will be available to the medical imaging scanner over the time period and/or the predicted instantaneous power that will be available to the medical imaging scanner during the time period.

In an example, a trained neural network is utilized by the processing unit to predict the total energy that will be available to the medical imaging scanner over the time period and to predict the instantaneous power that will be available to the medical imaging scanner during the time period; and/or a trained neural network is utilized by the processing unit to select the scan protocol for the medical imaging scanner to carry out the scan of the patient.

In an example, the trained neural network that predicts total energy and instantaneous energy availability is the same neural network that selects the scan protocol.

In an example, a trained neural network is utilized by the processing unit to predict the total energy and/or instantaneous power utilized by the medical imaging scanner for a scan and/or or a scan sequence of a scan protocol.

Therefore, the new technique is in effect a recommendation system that predicts the required energy for a diagnostic scan/therapeutic procedure and predicts the expected energy that will be available for the imaging system in the mobile and/or energy-wise instable location, enabling a scan protocol for that scan to be selected. In other words, safe scan planning using intelligent energy consumption and energy availability prediction allows for uninterrupted guaranteed diagnostic imaging quality using machine learning.

Thus, use is made of today's power and energy sources, that have some monitor and power distribution technology indicating the instantaneous power available and that anticipated to be available in the coming period. This is utilized along with an understanding of previous overall energy and power usage requirements made of the power and energy sources to build a new "energy aware" imaging support mechanism to plan in advance the clinical scans of a diagnostic system, such as a mobile scanner or a scanner in a rural area. Use is also made of the power and energy utilized by a medical scanner for individual scans and over a whole scan sequence of a scan protocol, provided from past actual scan data, or from reference or manufacturer information.

To put this a use is made of mobile power systems being able to predict their power output for the coming period and an understanding of power requirements made of the mobile power system to predict which scans could be finalized for the available energy or which scan conditions are compatible with the expected power setting at a given moment. In other words, the selection of the clinical scan protocol is made with respect to the required energy consumption is correlated to the expected available energy and power available.

Figure 4:
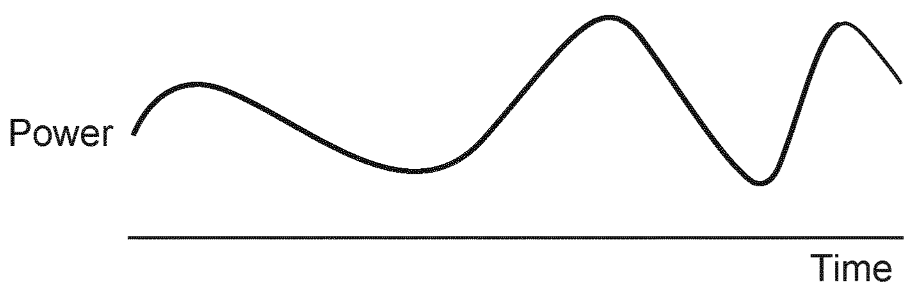
FIG. 4 shows a representation of a predicted power output from one or more power supplies that a medical imaging scanner will utilize during a scan.
Figure 5:
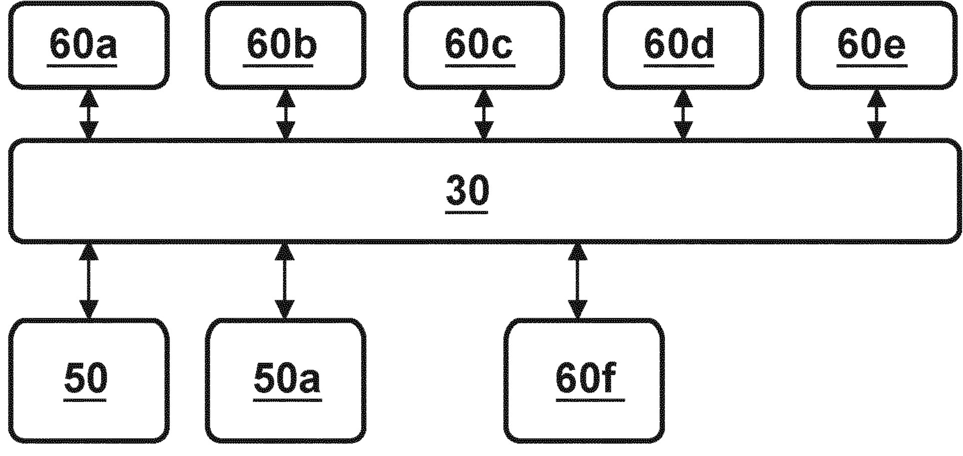
FIG. 5 shows a schematic representation of a detailed embodiment of a medical scan system.
Figure 6:
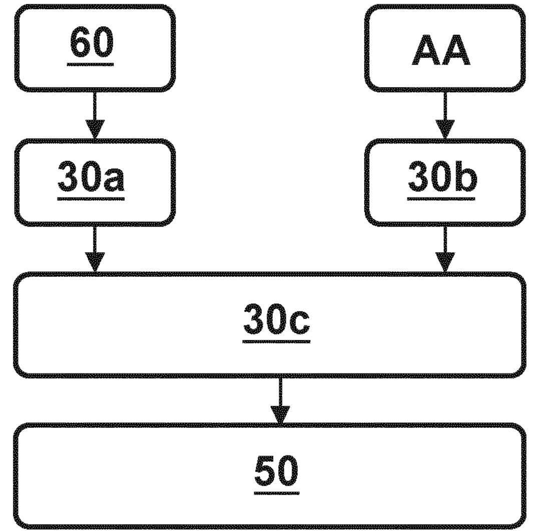
FIG. 6 shows a detailed flowchart for scan protocol selection for a medical scan system.

The medical scan apparatus, medical scan system, and medical scan method are now described in specific further detail, where reference is made to FIGS. 4-6.

The new technique in effect provides a recommendation system based on the prediction of the required energy for a diagnostic scan/therapeutic procedure and the expected energy to be available for the imaging system in the mobile and/or energy-wise instable location. Safe scan planning using intelligent energy consumption and energy availability prediction is enabled to allow for uninterrupted guaranteed diagnostic imaging quality using machine learning.

FIG. 4 shows an example of the predicted power output from power generating elements that will be used by a medical imaging scanner. This can be predicted based on what the power generating elements themselves predict their current power and energy provision is and what that will be into the near future, and based on an understanding of historical power provision from the power generating elements and whether what happened in the past (the link between weather and the requirement for air conditioning, AC, units to be activated) could occur in the near future. In FIG. 4 the predicted power output is shown as a power/time profile (see figure below). The line represents the instantaneous power available, and the total energy is the integral of the area under the curve.

It has been established that in general there will be two requirements which are used in the new technique to eliminate certain scans from a scan sequence in the situation of a limited power supply.

1. Total energy requirement: the total energy available for a given period (area under the curve of FIG. 4) must be sufficient to cover the total energy needs of the scan.
2. Instantaneous power: If requirement 1 is met, a second requirement is that the peak power of the scan cannot exceed the instantaneous peak power (the height of the curve of FIG. 4)

The new technique determines that scans which do not meet both criteria cannot be initiated in their reference form. However, there are certain technical features which can be considered to adapt the system such that the scan indeed meets both criteria. In other words, a reference scan can be changed in some way in order that it can meet the total energy and instantaneous power requirements.

These are discussed below.

Total energy:

The total scan can be slowed down so that the total energy (area under the curve) increases Less critical energy consuming parts of the system can be de-activated, whereby the energy to the system increases. Examples are climate conditioning, lighting, data processing, communication, vehicle systems etc.

If there is still insufficient total energy and/or insufficient instantaneous power, a determination can be made that additional energy sources must be activated Instantaneous power:

The section of the scan which draws too much power can be slowed down (e.g. gradients are reduced in MR, X-ray system anode power reduced in CT/DXR . . . ) in order that the instantaneous power decreases Less critical power consuming parts of the system can be temporarily de-activated, whereby the instantaneous power to the system increases. Examples are climate conditioning, lighting, data processing, communication, vehicle systems etc If there is still insufficient total energy and/or insufficient instantaneous power, a determination can be made that additional energy sources must be activated In this manner, the prospective planning and prediction of the expected energy helps to optimize the scanning protocols or even organize the patient sequence/hospital workflow.

FIG. 5 shows a schematic representation of a detailed embodiment of a medical scan system. In FIG. 5 there are a number of power sources 60. In FIG. 5 Solar is represented by 60*a*, Fuel cell is represented by 60*b*, Hydrogen tank is represented by 60*c*, DC is represented by 60*d*, AC is represented by 60*e*, and local charging is represented by 60*f*. The safe scan planning using intelligent energy consumption and energy availability prediction to allow for uninterrupted guaranteed diagnostic imaging quality is then carried out by a processing unit 30. This can be considered to be a state machine, with a smart grid software interface, that predicts energy and power availability and energy and power requirements, and that controls a medical imaging scanner 50 and/or a therapy device 50*a*.

Referring to FIG. 5, the new technique provides for the scan planning and scanning that takes the actual power condition and the backup power into consideration to ensure a safe and reliable imaging of the patient. The planning is based on historic data of the last days with typical network conditions and at the same time includes the short term (UPS) and mid term (generator) backup energy that could be used by the system. In addition the problems that occur during switching processes and network quality variations are considered and even measured effects can be used for image processing to compensate/identify artifacts but still allow for diagnostic quality. For longer scans—especially MRI and here especially mobile MRI—the available backup power information is used to do a safe scan planning for the most urgent patients. A sensor system monitors the power condition, which includes different sources of energy to allow for the intelligent load and power distribution based on the scan requests of the imaging system. This includes the DC network from battery buffered systems and solar systems as well as energy sources from a truck, ship, train etc in a mobile setting. In addition the fixed network supply and installed generator capacity is taken into account, and it is also taken into account fast generators could step in, the power they can provide, and how long it could operate. The sum of all these available power sources results in the power/time profile described above and shown in FIG. 4.

Continuing with FIG. 5, different energy sources are available and are connectable to a smart grid. The smart grid can be considered to be connected to or part of the processing unit 30 described above. The individual sources are active or passive and deliver energy during certain time intervals. The system is modular, as additional energy can be further connected at certain geographical locations (hospitals, parking, mobile power charging). The expected power and energy at a certain location at a defined time interval is provided by a machine learning algorithm.

Thus, diagnostic and therapeutically clinical systems are provided with appropriate power to carry out a selected scan, that can be supplied by mobile energy supplies and energy supplies in rural areas that may not have consistent power availability profiles. As discussed above, scans can be selected, which also refers to scan adaptation. In other words, a MRI/CT protocol is adapted with respect to the expected or real available energy, and different scans can be selected and combined so that required energy fits with the provided energy.

The new system can also optimize for a lowest energy consumption with respect to an accepted diagnostic imaging quality index. To do this, an MRI sequence can be adapted or a selection is made to stretch or delay a predicted scan sequence or session based on predicted energy consumption and predicted available rest energy or charging time or charging power.

The "just in time" availability of the required energy is enabled by the smart grid and is synchronized with the timeline of the imaging sequence. For example for a CT scan enough power has to be available at the timeframe when the high voltage generator provides power for the x-ray tube during the x-ray on time, while less power is required during patient preparation, scanner rotation and data processing. The new system takes this all into account when selecting the scan protocol.

FIG. 6 shows a flowchart for protocol selection. In FIG. 6 energy or power sources are represented by 60. The information from these sources is provided to a processing unit 30. The processing unit 30 can be considered to have a first element 30*a* that is a software machine learning part that predicts the energy availability from the energy or power sources 60. The processing unit 30 can be considered to have a second element 30*b* that is a software machine learning part that predicts the energy and power requirement for different clinical protocols, where information on clinical protocols and their energy consumption is provided to the processing unit 30 indicated as AA. The first and second software machine learning parts can be a single trained neural network or two separate trained neural networks. The processing unit 30 then has a further element indicated as 30*c* that determines/selects which scan protocol should be utilized for the scan based on the information derived from the first and second parts 30*a* and 30*b*. The scan protocol is then provided to a medical imaging scanner 50 to proceed to carry out the scan with this scan protocol, where a diagnostic scan or a therapy scan can be carried out.

Thus, with respect to FIG. 6 a recommendation system based on the prediction of the expected energy to be available for diagnostic imaging is shown. A software decision is made by machine learning using a trained network. Input parameters come from the different energy sources and the network delivers an expected energy index for a certain time interval at a certain geometrical location. Additionally, suitable MRI protocols are recommended/selected to/for operators on mobile diagnostic vehicles and in rural locations. This addresses an important issue and clinical need, enabling to operate these systems in rural and locations with no or low energy delivery, where predictions and recommendations are calculated from the energy consumption predicted by a trained neuronal network ML constructed by input data of clinical sequences (X-Ray MRI) and/or therapy (Hyperthermia, ablation, radiation therapy and combinations of those). These are provided only as examples.

The following describes several detailed embodiments, placing the new technique into context.

Embodiment 1

A compact system is optimized for a truck with a mobile imaging system using the generator power and short term additional battery based energy buffers. Other energy consuming systems can be automatically switched off during the critical scan times to ensure completing the diagnostic scan.

Embodiment 2

A Hospital in a rural area with unstable power network and changing power availability during the different times of the day. The history based learning of the AI system can predict the estimated available power condition during the planned timeslot for the patient's scan. In the situation where there is not enough available energy from the network the algorithm proposes different options based on calculated risks and times.

- The sequence of the scans could be adapted to ensure that the most critical scans can be done with high confidence.
- The protocols of one or more scans can be adapted to still get the most relevant diagnostic information for all patients, but limiting the acquisition of "not so relevant additional data" that would normally preferably be acquired, but is not essential
- The system can activate auxiliary energy sources at dedicated times and/or at least to prepare in standby modes to minimize the risk of system shutdown
- The system can activate and switch on auxiliary energy sources like battery buffer, generator, and switch off unnecessary other devices.

Embodiment 3

A software interface from the energy prediction unit (the appropriate functionality of the processing unit 30 as discussed above) (which is equipped with energy logging functionality to provide information about available energy at a certain time including backup energy) is connected to the hospital IT. The information from the interface can be used to adapt the workflow with the patient sequence, predict patient planning per dedicated day/time linked to the patient specific imaging/treatment where the patient specific imaging/treatment has additional information about the required energy as information power over time. The information can be linked to weather prediction information in case of solar based power generation (main or additional energy) but also to estimate energy consumption and stability of the power network (in case many air-condition systems will consume lots of energy due to heat at certain days/times).

Embodiment 4: Total Energy Versus Instantaneous Power

To reduce instantaneous power, a MRI system can switch the RF power amplifier from high to low peak power mode. The system is configured such that the transmit chain can automatically switch between system integrated transmit antenna to local transmit/receive antenna, which needs lower peak excitation power. Typically a MRI imaging diagnostic session consists of a sequence of individual scans with different peak/average power ratio. A scan with a high average power can be stopped and a required time period of the rest of scan is shifted to a more favorable position with respect to total available energy. Thus individual scans can be divided and distributed to compatible energy periods. A therapy device such as a MR Linac or a hyperthermia system does have a controller to calculate the required total Energy versus instantaneous power and the new system can interact with this to ensure that a final required dose is achieved at the end of the session.

For DXR and CT systems with an x-ray tube, the main power consumption is related to the x-ray generation and the generated heat due to the low efficiency of the x-ray generation principle. 99% of the energy will lead to heating up of the x-ray tube, the housing and the thermal load has to be cooled down to enable continuous operation. Options to adapt the diagnostic scan with respect to the available energy are trade-offs for the exact scan time, the maximum power, the cooling capacity and the x-ray detection system that can be operated synchronized to the x-ray on time. Therefore, in case of low energy availability at a certain time, but expected higher energy availability at a short time period later, the times of the scout scan and the diagnostic scan can be adapted to the main energy profile and the required energy level will trigger the energy buffer connection. The scan parameter, the cooling rate and related cooling down time can be adapted to the energy availability profile. In addition, extra stand-by operation of the detector and data acquisition system can reduce the constant power consumption (under consideration of required conditions for stable image quality-no temperature gradients for the detector). For short time-high intensity scans-an additional energy buffer helps to deliver peak power and the limited buffer energy will be integrated in an optimized time profile with pre-knowledge about the scan sequence and the exact scan profile of the patient leading to x-ray intensity modulation and with that to modulation of the required energy.

In another exemplary embodiment, a computer program or computer program element is provided that is characterized by being configured to execute the method steps of any of the methods according to one of the preceding embodiments, on an appropriate apparatus or system.

The computer program element might therefore be stored on a computer unit, which might also be part of an embodiment. This computing unit may be configured to perform or induce performing of the steps of the method described above. Moreover, it may be configured to operate the components of the above described system. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, USB stick or the like, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A medical scan apparatus, comprising:

a memory that stores a plurality of instructions; and a processor coupled to the memory and configured to execute the plurality of instructions to:

obtain information regarding the power production capability of one or more power sources, and wherein a scan of a patient to be carried out by a medical imaging scanner utilizes at least the one or more power sources;

predict the total energy that will be available to the medical imaging scanner over a time period, wherein the prediction comprises utilization of the information regarding the power production capability of the one or more power sources;

predict the instantaneous power that will be available to the medical imaging scanner during the time period of the scan, wherein the prediction comprises utilization of the information regarding the power production capability of the one or more power sources;

select a scan protocol for the medical imaging scanner to carry out the scan of the patient, wherein selection of the scan protocol comprises utilization of the predicted total energy that will be available to the medical imaging scanner over the time period and/or the predicted instantaneous power that will be available to the medical imaging scanner during the time period of the scan, wherein selection of the scan protocol comprises a selected ordering of steps of the scan, wherein selection of the scan protocol comprises a modification of one or more steps of the scan; and provide the scan protocol to the medical imaging scanner.

2. The apparatus according to claim 1, wherein the processor is configured to predict the total energy and/or instantaneous power utilized by the medical imaging scanner for the scan and/or a scan sequence of a scan protocol.

3. The apparatus according to claim 1, wherein the processor is configured to obtain information regarding the total energy and/or instantaneous power utilized or required by the medical imaging scanner for the scan and/or a scan sequence of a scan protocol.

4. The apparatus according to claim 1, wherein the information regarding the power production capability of the one or more power sources comprises the instantaneous power production capability of one or more power sources.

5. The apparatus according to claim 1, wherein the information regarding the power production capability of the one or more power sources comprises historical instantaneous power production capability of the one or more power sources.

6. The apparatus according to claim 1, wherein the processor is configured to obtain weather forecast information, wherein the prediction of the total energy that will be available to the medical imaging scanner over the time period comprises utilization of the weather forecast information, and wherein the prediction of the instantaneous power that will be available to the medical imaging scanner during the time period comprises utilization of the weather forecast information; and/or wherein the processor is configured to obtain historical weather information, wherein the prediction of the total energy that will be available to the medical imaging scanner over the time period comprises utilization of the historical weather information, and wherein the prediction of the instantaneous power that will be available to the medical imaging scanner during the time period comprises utilization of the historical weather information.

7. The apparatus according to claim 1, wherein the processor is configured to determine that an additional power source to the one or more power sources will be required to be utilized by the medical imaging scanner to carry out the scan of the patient, wherein the determination comprises utilization of predicted total energy that will be available to the medical imaging scanner over the time period and/or the predicted instantaneous power that will be available to the medical imaging scanner during the time period.

8. The apparatus according to claim 1, wherein the processor is configured to determine that a power drain will be required to be disconnected from the one or more power sources during the time period, wherein the determination comprises utilization of predicted total energy that will be available to the medical imaging scanner over the time period and/or the predicted instantaneous power that will be available to the medical imaging scanner during the time period.

9. The apparatus according to claim 1, wherein a trained neural network is utilized by the processor to predict the total energy that will be available to the medical imaging scanner over the time period and/or to predict the instantaneous power that will be available to the medical imaging scanner during the time period; and/or wherein a trained neural network is utilized by the processor to select the scan protocol for the medical imaging scanner to carry out the scan of the patient.

10. A computer-implemented medical scan method, comprising:

providing information regarding the power production capability of one or more power sources, and wherein a scan of a patient to be carried out by a medical imaging scanner will utilize at least the one or more power sources;

predicting the total energy that will be available to the medical imaging scanner over a time period, wherein the predicting comprises utilizing the information regarding the power production capability of the one or more power sources;

predicting the instantaneous power that will be available to the medical imaging scanner during the time period, wherein the predicting comprises utilizing the information regarding the power production capability of the one or more power sources;

selecting a scan protocol for the medical imaging scanner to carry out the scan of the patient, wherein selecting the scan protocol comprises utilizing the predicted total energy that will be available to the medical imaging scanner over the time period of the scan and/or the predicted instantaneous power that will be available to the medical imaging scanner during the time period of the scan; wherein selecting the scan protocol comprises selecting an order of steps of the scan; wherein selecting the scan protocol comprises modifying one or more steps of the scan; and providing the scan protocol to the medical imaging scanner.

11. A non-transitory computer-readable medium comprising executable instructions which, when executed by at least one processor, cause the at least one processor to perform a medical scan method, the method comprising:

providing information regarding the power production capability of one or more power sources, and wherein a scan of a patient to be carried out by a medical imaging scanner will utilize at least the one or more power sources;

predicting the total energy that will be available to the medical imaging scanner over a time period, wherein the predicting comprises utilizing the information regarding the power production capability of the one or more power sources;

predicting the instantaneous power that will be available to the medical imaging scanner during the time period, wherein the predicting comprises utilizing the information regarding the power production capability of the one or more power sources;

selecting a scan protocol for the medical imaging scanner to carry out the scan of the patient, wherein selecting the scan protocol comprises utilizing the predicted total energy that will be available to the medical imaging scanner over the time period of the scan and/or the predicted instantaneous power that will be available to the medical imaging scanner during the time period of the scan, wherein selecting the scan protocol comprises selecting an order of steps of the scan, and wherein selecting the scan protocol comprises modifying one or more steps of the scan; and providing the scan protocol to the medical imaging scanner.

* * * * *